United States Patent
Berthoud et al.

(10) Patent No.: US 9,862,736 B2
(45) Date of Patent: Jan. 9, 2018

(54) BIMETALLIC COMPLEX COMPRISING CYCLOPENTADIENYL AND AMIDINE LIGANDS

(71) Applicant: LANXESS Elastomers B.V., Geleen (NL)

(72) Inventors: Alexandra Berthoud, Neeharen (BE); Victor Quiroga Norambuena, Lanaken (BE); Gerard Van Doremaele, Sittard (NL); Martin Alexander Zuideveld, Kelmis (BE); Henricus Johannes Arts, Munstergeleen (NL); Richard Thomas William Scott, Maastricht (NL)

(73) Assignee: ARLANXEO NETHERLANDS B.V., Geleen (NL)

( * ) Notice: Subject to any disclaimer, the term of this patent is extended or adjusted under 35 U.S.C. 154(b) by 155 days.

(21) Appl. No.: 14/898,500

(22) PCT Filed: Jun. 18, 2014

(86) PCT No.: PCT/EP2014/062783
§ 371 (c)(1),
(2) Date: Dec. 15, 2015

(87) PCT Pub. No.: WO2014/202644
PCT Pub. Date: Dec. 24, 2014

(65) Prior Publication Data
US 2016/0122370 A1 May 5, 2016

(30) Foreign Application Priority Data

Jun. 18, 2013 (EP) .................................. 13172492

(51) Int. Cl.
*C07F 17/00* (2006.01)
*C08F 4/6592* (2006.01)
(Continued)

(52) U.S. Cl.
CPC .............. *C07F 7/28* (2013.01); *C07C 257/18* (2013.01); *C07F 17/00* (2013.01); *C08F 4/6592* (2013.01); *C08F 4/65908* (2013.01); *C08F 4/65912* (2013.01); *C08F 210/02* (2013.01); *C08F 210/16* (2013.01); *C08F 210/18* (2013.01); *C08F 2410/03* (2013.01)

(58) Field of Classification Search
CPC ................ C08F 4/6592; C08F 4/65908; C08F 4/65912; C08F 10/06
See application file for complete search history.

(56) References Cited

U.S. PATENT DOCUMENTS 7,956,140 B2 6/2011 Ijpeij et al.

FOREIGN PATENT DOCUMENTS

WO 2005090418 9/2009

OTHER PUBLICATIONS

Delferro, M., et al. "Multinuclear Olefin Polymerization Cataysts", Chem. Rev., vol. 111, pp. 2450-2485 (2011).
Chen, E. "Cocatalysts for Metal-Catalyzed Olefin Polymerization: Activators, Activation Processes, and Structure-Activity Relationships", Chem. Rev. 2000, vol. 100, pp. 1391-1434 (2000).
Izvestiya Akademi Nauk, Seriya Khimicheskaya, "BIS-(N2-Hydroxyhexafluoroisopropyl-N1, N1-Substituted) Terephthalamidines and their reaction with perfluorohexanecarbonitrile", A.N. Nesmeyanov Institute of Heteroorganic Compounds, No. 7, pp. 1616-1619 (1990).
Li, et al., "Study on the Synthesis and Structure of Diphenylphosphine Oxide and Lithium Phosphine Coordination Polymer", Journal of Shanxi Univeristy (Nat. Sci. Ed.) 31(4), 561-564; 2008.

(Continued)

Primary Examiner — Caixia Lu (57) ABSTRACT

The present invention relates to a new bimetallic complex of the formula (1) wherein: M is a group 4-6 metal $R^1$ means is a substituent comprising a heteroatom of group 15, through which $R^1$ is bonded to the imine carbon atom; $R^2$-$R^6$ are the same or different and each represents a hydrogen atom, an optionally substituted C1-10 alkyl group, an optionally substituted C1-10 alkoxy group, an optionally substituted C6-20 aryl group, an optionally substituted C6-20 aryloxy group, an optionally substituted C7-20 aralkyl group, an optionally substituted C7-20 aralkyloxy group, a silyl group substituted with optionally substituted C1-20 hydrocarbon group(s), a C1-20 hydrocarbon-substituted amino group or the adjacent $R^2$-$R^6$ may be linked to each other to form a ring; $R^7$-$R^{10}$ are the same or different and each represents a hydrogen atom, a halogen atom, an optionally substituted C1-10 alkyl group, an optionally substituted C1-10 alkoxy group, an optionally substituted C6-20 aryl group, an optionally substituted C6-20 aryloxy group, an optionally substituted C7-20 aralkyl group, an optionally substituted C7-20 aralkyloxy group, a silyl group substituted with optionally substituted C1-20 hydrocarbon group(s), a C1-20 hydrocarbon-substituted amino group or the adjacent $R^7$-$R^{10}$ may be linked to each other to form a ring; L is an optional neutral Lewis basic ligand, and j is an integer denoting the number of neutral ligands L; and X is an anionic ligand, and r is an integer denoting the number of anionic ligands X and wherein the two cyclopentadienyl-amidinato-metal-containing moieties as in the brackets are the same or different.

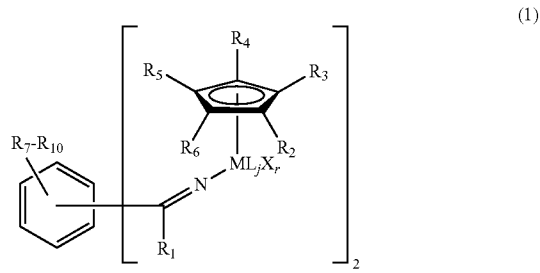

(1)

17 Claims, 4 Drawing Sheets (51) Int. Cl.
   *C08F 210/16*   (2006.01)
   *C08F 210/18*   (2006.01)
   *C07F 7/28*     (2006.01)
   *C08F 4/659*    (2006.01)
   *C07C 257/18*   (2006.01)
   *C08F 210/02*   (2006.01)

(56) References Cited

OTHER PUBLICATIONS

International Search Report in corresponding application No. PCT/EP2014/062783 (3 pages) (2014).
Edwin G. Ipeij et al., "Synthesis, solid sate and DFT structure and olefin polymerization capability of a unique base-free dimeric methyl titantium dication", The Royal Society of Chemistry 2010, Chem. Commun., 46, 3339-3341 (2010).
Schelter et al., "1, 4-Dicyanobenzene as a scaffold for the preparation of bimetallic actinide complexes exhibiting metal-metal communication", Chemistry, a European Journal, vol. 14, No. 26, pp. 7782-7790 (2008).

Figure 1 – X-ray picture of compound 1

Figure 2 – X-ray picture of compound 2

Figure 3 – X-ray picture of compound 3

Figure 4 – X-ray picture of compound 4

BIMETALLIC COMPLEX COMPRISING CYCLOPENTADIENYL AND AMIDINE LIGANDS

The present invention relates to a bimetallic complex containing a cyclopentadienyl and amidine ligand, a process for its preparation, a precursor, a catalyst system containing said metal complex and a process for manufacturing polymers wherein said metal complex or catalyst system is used.

A process for the polymerization of at least one olefin having 2 to 8 carbon atoms in the presence of a polymerization catalyst component comprising an amidine ligand, an activator, and optionally a scavenger is known from WO2005090418. WO2005090418 discloses a process for the copolymerization of ethylene and at least one additional alpha olefin having from 3 to 8 carbon atoms characterized in that said process employs a catalyst system for olefin polymerization comprising an organometallic complex of a group 4 metal comprising an amidine ligand, an activator and an optional scavenger. WO2005090418 discloses also a process for the copolymerisation of ethylene, alpha olefin and one or more non-conjugated dienes.

An advantage of the polymer comprising the monomeric units of 5-vinyl-2-norbornene (VNB) is that it cures rapidly when using a peroxide as a curative. For that reason it is desirable to use this polymer in rubber composition suitable for peroxide curing, like for instance rubber compositions used for the production of cable and wire, hoses for automotive applications; like for instance radiator hoses and hoses used in the braking system, thermoplastic elastomers and a wide variety of further rubber applications.

A serious disadvantage however is that in the production of the polymer comprising the 5-vinyl-2-norbornene (VNB) using one of the known processes is that a high degree of long-chain branching can be formed in the polymer and gelation of the polymer can occur as a result. This branching also leads to broadening of the molecular weight distribution. This is a disadvantage for the mechanical properties of a rubber comprising the polymer. If gelation occurs the polymer is partly or entirely cross-linked. The gelation is disadvantageous since it can cause the polymerization process to be unstable, reactor fouling to take place and the polymer to be not useful for use in a rubber composition intended for the production of shaped articles.

Bimetallic catalyst components for the polymerization of olefins are known in the art and well documented in various reviews such as in Chem. Rev. 2011, 111, 2450-2485. The propensity of such bimetallic catalysts to display so-called cooperative effects which can influence polymer properties such as long chain branching are well known. According to this review article it may be expected that the influence of such cooperative effects would be to increase the degree of long chain branching which may be disadvantageous as described above.

A purpose of the invention is to provide a new class of bimetallic catalyst components comprising bis-amidine type ligands which could be prepared easily with a synthesis compatible with more bulky substituents. Surprisingly and advantageously these bimetallic catalyst components incorporate non-conjugated dienes, such as VNB, whilst displaying decreased long chain branching properties than for the monometallic catalyst components in the known process embodied in WO2005090418.

DETAILS OF THE INVENTION

This objective is achieved with a bimetallic complex of the formula (1)

wherein:
M is a group 4-6 metal
$R^1$ is a substituent comprising a heteroatom of group 15, through which $R^1$ is bonded to the imine carbon atom;
$R^2$-$R^6$ are the same or different and each represents a hydrogen atom, an optionally substituted C1-10 alkyl group, an optionally substituted C1-10 alkoxy group, an optionally substituted C6-20 aryl group, an optionally substituted C6-20 aryloxy group, an optionally substituted C7-20 aralkyl group, an optionally substituted C7-20 aralkyloxy group, a silyl group substituted with optionally substituted C1-20 hydrocarbon group(s), a C1-20 hydrocarbon-substituted amino group or the adjacent $R^2$-$R^6$ may be linked to each other to form a ring;
$R^7$-$R^{10}$ are the same or different and each represents a hydrogen atom, a halogen atom, an optionally substituted C1-10 alkyl group, an optionally substituted C1-10 alkoxy group, an optionally substituted C6-20 aryl group, an optionally substituted C6-20 aryloxy group, an optionally substituted C7-20 aralkyl group, an optionally substituted C7-20 aralkyloxy group, a silyl group substituted with optionally substituted C1-20 hydrocarbon group(s), a C1-20 hydrocarbon-substituted amino group or the adjacent $R^7$-$R^{10}$ may be linked to each other to form a ring;
L is an optional neutral Lewis basic ligand, and j is an integer denoting the number of neutral ligands L; and
X is an anionic ligand, and r is an integer denoting the number of anionic ligands X
wherein the two cyclopentadienyl-amidinato-metal-containing moieties as in the brackets are the same or different, preferably they are the same.

The following meaning of the substituents are given for each cyclopentadienyl-amidinato-metal-containing moiety independently.

M
In a preferred embodiment the metal M of group 4 is titanium (Ti), zirconium (Zr) or hafnium (Hf), most preferably titanium (Ti).

$R^1$
In a preferred embodiment of the present invention relates to a metal complex of the formula (1) wherein $R^1$ is of the general formula —$NR^{11}R^{12}$ with $R^{11}$ and $R^{12}$ being individually selected from the group of aliphatic C1-10 hydrocarbyl, halogenated aliphatic C1-10 hydrocarbyl, aromatic C6-20 hydrocarbyl and halogenated C6-20 aromatic hydrocarbonyl residues. $R^{11}$ optionally forming a heterocyclic structure with $R^{12}$ or with either one of the radicals $R^7$ to $R^{10}$. Preferred examples for $R^1$ are dimethylamide, diisopropylamide, biscyclohexyl amide, and N-dimethylphenyl N-ethylamide.

The two amidine moieties of formula 1 may be ortho-, meta- or para- to one another with respect to the aryl ring. Preferably these groups are meta- or para- to one another.

Substituents

Specific examples of the optionally substituted C1-10 alkyl group for the substituents $R^2$ to $R^{10}$ and the radical X include a methyl group, an ethyl group, a n-propyl group, an isopropyl group, a n-butyl group, a sec-butyl group, a tert-butyl group, a n-pentyl group, a neopentyl group, an amyl group, a n-hexyl group, a n-octyl group and a n-decyl group. Furthermore, the above substituents which are substituted with halogen atom(s) (especially fluorine atom(s)) are exemplified, and specific examples thereof include a fluoromethyl group, a difluoromethyl group, a trifluoromethyl group, a fluoroethyl group, a difluoroethyl group, a trifluoroethyl group, a tetrafluoroethyl group, a pentafluoroethyl group, a perfluoropropyl group, a perfluorobutyl group, a perfluoropentyl group, a perfluorohexyl group, a perfluorooctyl group, a perfluorodecyl group, a trichloromethyl group, and the like. Among these, a methyl group, an ethyl group, an isopropyl group, a tert-butyl group, an amyl group and the like are preferred.

The optionally substituted C6-20 aryl group for $R^2$ to $R^{10}$ and the radical X include a phenyl group, a naphthyl group, an anthracenyl group and the like, and specific examples thereof include, for example, a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetra-methylphenyl group, a 2,3,5,6-tetramethylphenyl group, a pentamethylphenyl group, an ethylphenyl group, a n-propylphenyl group, a isopropylphenyl group, a n-butylphenyl group, a sec-butylphenyl group, a tertbutylphenyl group, a n-pentylphenyl group, a neopentylphenyl group, a n-hexylphenyl group, a n-octylphenyl group, a n-decylphenyl group, a n-dodecylphenyl group, a n-tetradecylphenyl group, a naphthyl group, and an anthracenyl group. Furthermore, the above substituents which are substituted, for example, with halogen atom(s), more specifically with fluorine atom(s), are exemplified. As preferable aryl group, a phenyl group is exemplified.

The optionally substituted C7-20 aralkyl group of $R^2$ to $R^{10}$ and the radical X include a benzyl group, a naphthylmethyl group, an anthracenylmethyl group, a diphenylmethyl group, a diphenylmethyl group and the like, and specific examples thereof include, for example, a benzyl group, a (2-methylphenyl)methyl group, a (3-methylphenyl)methyl group, a (4-methyl-phenyl)methyl group, a (2,3-dimethylphenyl)methyl group, a (2,4-dimethyl-phenyl)methyl group, a (2,5-dimethylphenyl)methyl group, a (2,6-dimethylphenyl)methyl group, a (3,4-dimethylphenyl)methyl group, a (2,3,4-trimethylphenyl)methyl group, a (2,3,5-trimethylphenyl)methyl group, a (2,3,6-trimethylphenyl)methyl group, a (3,4,5-trimethylphenyl)methyl group, a (2,4,6-trimethylphenyl)methyl group, a (2,3,4,5-tetramethylphenyl)methyl group, a (2,3,4,6-tetramethylphenyl)methyl group, a (2,3,5,6-tetramethylphenyl)methyl group, a (pentamethylphenyl)methyl group, an (ethyl-phenyl)methyl group, a (n-propyl-phenyl)methyl group, an (isopropylphenyl)methyl group, a (n-butylphenyl)methyl group, a (sec-butylphenyl)methyl group, a (tert-butylphenyl)methyl group, a (n-pentylphenyl)methyl group, a (neopentylphenyl)methyl group, a (n-hexylphenyl)methyl group, a (n-octylphenyl)methyl group, a (n-decyl-phenyl)methyl group, a (n-dodecylphenyl)methyl group, a naphthylmethyl group, an anthracenylmethyl group, a diphenylmethyl group, and the above substituents substituted by halogen, more specifically, a fluorine-substituted aralkyl group. A benzyl group is exemplified as a preferable substituent.

Specific examples of the optionally substituted C1-10 alkoxy group for the substituents $R^2$ to $R^{10}$ and the radical X include a methoxy group, an ethoxy group, a n-propoxy group, an isopropoxy group, a n-butoxy group, a sec-butoxy group, a tert-butoxy group, a n-pentyloxy group, a neopentyloxy group, a n-hexyloxy group, a n-octyloxy group, a n-nonyloxy group, and a n-decyloxy group. Furthermore, the alkoxy groups substituted with halogen(s) are exemplified, and more specifically, a fluorine atom-substituted alkoxy group, in which the alkoxy group is substituted with fluorine atom(s), is exemplified. Preferably, a methoxy group, an ethoxy group, and a tert-butoxy group are exemplified.

The optionally substituted C6-20 aryloxy group for the substituents $R^2$ to $R^{10}$ and the radical X includes a phenoxy group, a naphthoxy group, and an anthracenoxy group. Furthermore, specific examples thereof include a phenoxy group, a 2-methylphenoxy group, a 3-methylphenoxy group, a 4-methylphenoxy group, a 2,3-dimethylphenoxy group, a 2,4-dimethylphenoxy group, a 2,5-dimethylphenoxy group, a 2,6-dimethylphenoxy group, a 3,4-dimethylphenoxy group, a 3,5-dimethylphenoxy group, a 2,3,4-trimethylphenoxy group, a 2,3,5-trimethylphenoxy group, a 2,3,6-trimethylphenoxy group, a 2,4,5-trimethylphenoxy group, a 2,4,6-trimethylphenoxy group, a 3,4,5-trimethylphenoxy group, a 2,3,4,5-tetramethylphenoxy group, a 2,3,4,6-tetramethylphenoxy group, a 2,3,5,6-tetramethylphenoxy group, a pentamethylphenoxy group, an ethylphenoxy group, a n-propylphenoxy group, an isopropylphenoxy group, a n-butylphenoxy group, a sec-butylphenoxy group, a tert-butylphenoxy group, a n-hexyl-phenoxy group, a n-octylphenoxy group, a n-decylphenoxy group, a n-tetradecylphenoxy group, a naphthoxy group, an anthracenoxy group, and the above substituents substituted with halogen atom(s), and more specifically, a fluorine-substituted aryloxy group is exemplified. The optionally substituted C7-20 aralkyloxy group for the substituents $R^2$ to $R^{10}$ and the radical X include a benzyloxy group, a naphthylmethoxy group, an anthracenylmethoxy group, and a diphenylmethoxy group. Furthermore, specific examples thereof include, for example, a benzyloxy group, a (2-methylphenyl)methoxy group, a (3-methyl-phenyl)methoxy group, a (4-methylphenyl)methoxy group, a (2,3-dimethylphenyl)-methoxy group, a (2,4-dimethylphenyl)methoxy group, a (2,5-dimethylphenyl)methoxy group, a (2,6-dimethylphenyl)methoxy group, a (3,4-dimethylphenyl)methoxy group, a (2,3,4-trimethylphenyl)methoxy group, a (2,3,5-trimethylphenyl)methoxy group, a (2,3,6-trimethylphenyl)methoxy group, a (3,4,5-trimethylphenyl)methoxy group, a (2,4,6-trimethylphenyl)methoxy group, a (2,3,4,5-tetramethylphenyl)methoxy group, a (2,3,4,6-tetramethylphenyl)methoxy group, a (2,3,5,6-tetramethylphenyl)methoxy group, a (pentamethylphenyl)methoxy group, an (ethylphenyl)methoxy group, a (n-propylphenyl)methoxy group, an (isopropylphenyl)methoxy group, a (n-butylphenyl)-methoxy group, a (sec-butylphenyl)methoxy group, a (tert-butylphenyl)methoxy group, a (n-pentylphenyl)methoxy group, a (neopentylphenyl)methoxy group, a (n-hexyl-phenyl)methoxy group, a (n-octylphenyl)methoxy group, a (n-decylphenyl)methoxy group, a (n-dodecylphenyl)methoxy group, a naphthylmethoxy group, an anthracenyl-methoxy group, a diphenylmethoxy group and the above substituents substituted with halogen(s), and more specifically, a fluorine atom-substituted aralkyloxy group is exemplified. A benzyloxy group is exemplified as a preferable substituent.

The C1-20 hydrocarbon-substituted silyl group for the substituents $R^2$ to $R^{10}$ and the radical X is a silyl group substituted with C1-20 hydrocarbon group(s). The hydrocarbon group as used herein includes, for example, C1-10 alkyl groups such as a methyl group, an ethyl group, a n-propyl group, an isopropyl group, a n-butyl group, a sec-butyl group, a tert-butyl group, a n-pentyl group, a neopentyl group, an amyl group, a n-hexyl group, a cyclohexyl group, a n-octyl group, a n-decyl group and the like, and C6-20 aryl groups such as a phenyl group, a tolyl group, a xylyl group, a naphthyl group, an anthracenyl group and the like. Such C1-20 hydrocarbon-substituted silyl group includes, for example, mono-substituted silyl groups such as a methylsilyl group, an ethylsilyl group, a phenylsilyl group and the like, di-substituted silyl groups such as a dimethylsilyl group, a diethylsilyl group, a diphenylsilyl group and the like, tri-substituted silyl groups such as a trimethylsilyl group, a triethylsilyl group, a tri-n-propylsilyl group, a tri-isopropylsilyl group, a tri-n-butylsilyl group, a tri-sec-butylsilyl group, a tri-tert-butylsilyl group, a tri-isobutylsilyl group, a tert-butyldimethylsilyl group, a tri-n-pentylsilyl group, a tri-n-hexylsilyl group, a tricyclohexylsilyl group, a triphenylsilyl group and the like, preferably a trimethylsilyl group, a tert-butyldimethylsilyl group, and a triphenylsilyl group. Furthermore, the above substituted silyl groups in which the hydrocarbon groups are substituted with halogen atom(s), e.g., fluorine atom(s), are exemplified.

The C1-20 hydrocarbon-substituted amino group for the substituents $R^2$ to $R^{10}$ and the radical X preferably is an amino group substituted with two hydrocarbon groups. The hydrocarbon group as used herein includes, for example, C1-10 alkyl groups such as a methyl group, an ethyl group, a n-propyl group, an isopropyl group, a n-butyl group, a sec-butyl group, a tert-butyl group, a n-pentyl group, a neopentyl group, an amyl group, a n-hexyl group, a cyclohexyl group, a n-octyl group, a n-decyl group and the like, and C6-20 aryl groups such as a phenyl group, a tolyl group, a xylyl group, a naphthyl group, an anthracenyl group and the like. Such C1-20 hydrocarbon-substituted amino group includes, for example, a dimethylamino group, a diethylamino group, a di-n-propylamino group, a diisopropylamino group, a di-n-butylamino group, a di-sec-butylamino group, a di-tert-butylamino group, a di-isobutylamino group, a tert-butylisopropylamino group, a di-n-hexylamino group, a di-n-octylamino group, a di-n-decylamino group, a diphenylamino group and the like, preferably, a dimethylamino group and a diethylamino group.

The halogen atom for the substituents $R^2$ to $R^{10}$ and the radical X include a fluorine atom, a chlorine atom, a bromine atom and an iodine atom, preferably a fluorine atom and a chlorine atom.

$R^2$-$R^6$

In a preferred embodiment $R^2$-$R^6$ are the same or different and each represents a hydrogen atom or a C1-5 alkyl group, in particular each represents methyl.

$R^7$-$R^{10}$

In a preferred embodiment $R^7$-$R^{10}$ are the same or different and each represents a hydrogen atom.

X

In a preferred embodiment X means a halogen atom, a C1-10 alkyl group, a C7-20 aralkyl group, a C6-20 aryl group or a C1-20 hydrocarbon-substituted amino group, and more preferably, a halogen atom and a C1-10 hydrocarbon-substituted amino group, most preferably Cl, F, Br, methyl, benzyl, methyltrimethylsilyl, phenyl, methoxyphenyl, di methoxyphenyl, N,N-dimethylaminophenyl, bis-(N,N-dimethylamino)phenyl, fluorophenyl, difluorophenyl, trifluorophenyl, tetrafluoropheny, perfluorophenyl, trialkylsilyl-phenyl, bis(trialkylsilyl)phenyl and tris(trialkylsilyl)phenyl. Most preferred are Cl or methyl. In case of more than one X the given meanings are independently.

r

The number of anionic ligands X is denoted as r and depends on the valency of the metal and the valency of the anionic ligand. Whereas the valency of the Group 5 and 6 metals can be as high as 6+, the preferred catalyst metals are Group 4 metals in their highest oxidation state (i.e. 4+) and the preferred anionic ligands X are monoanionic (such as a halogen or a hydrocarbyl group—especially methyl and benzyl). Thus, the preferred catalyst component contains a cyclopentadienyl ligand, an amidine ligand and two X, for instance chloride (or methyl) ligands bonded to the Group 4 metal. In contrast, the highest oxidation state of Group 5 and 6 metals are 5+ and 6+ respectively and will require a higher number or a higher anionic ligand valency to fulfill the electronic requirements. In some instances, the metal of the catalyst component may not be in the highest oxidation state. For example, a titanium (III) component would contain only one anionic ligand and a titanium (IV) component would contain 2 anionic ligands X.

L

Preferred is a metal complex of the formula (1) wherein L is an ether, a thioether, a amine, a tertiary phosphane, an imine, a nitrile, an isonitrile, or a bi- or oligodentate donor.

If more than one ligand L is present they may have different meanings.

The number "j" of neutral ligands in the metal complex of formula (1) may range from 1 to the amount that satisfies the 18-electron rule, as known in the art. Preferably from 1 to 2. In the preferred embodiment the number of neutral ligands L is zero.

Suitable ethers are diethyl ether, dipropyl ether, diisopropyl ether, dibutyl ether, dihexyl ether, anisole, phenetole, butyl phenyl ether, methoxytoluene, benzyl ethyl ether, diphenyl ether, dibenzyl ether, veratrole, 2-epoxypropane, dioxane, trioxane, furan, 2,5-dimethylfuran, tetrahydrofuran, tetrahydropyrane, 1,2-diethoxyethane, 1,2-dibutoxyethane, and crown ethers. Suitable thioethers are dimethyl sulfide, diethyl sulfide, thiophene, and tetrahydrothiophene. Suitable amines such as methylamine, dimethylamine, trimethylamine, ethylamine, diethylamine, triethylamine, propylamine, diisopropylamine, butylamine, isobutylamine, dibutylamine, tributylamine, pentylamine, dipentylamine, tripentylamine, 2-ethylhexylamine, allylamine, aniline, N-methylaniline, N,N-dimethylaniline, N,N-diethylaniline, toluidine, cyclohexylamine, dicyclohexylamine, pyrrole, piperidine, pyridine, picoline, 2,4-lutidine, 2,6-lutidine, 2,6-di(t-butyl)pyridine, quinoline, and isoquinoline, preferably tertiary amines such as trialkylamines, pyridine, bipyridine, tetramethylethylenediamine (TMEDA), and (−)-sparteine). Suitable tertiary phosphanes are triphenylphoshine and trialkylphosphanes. Suitable of imines are ketimines, guanidines, iminoimidazolidines, phosphinimines and amidines. Suitable bidentate ligands are diimines, alkyl or aryldiphoshanes, dimethoxyethane. Suitable oligodentate ligands are triimines (such as tris(pyrazolyl)alkanes), cyclic multidentate ligands comprising heteroatoms of group 13-17, including crown ethers optionally having heteroatoms of group 13-17, azo-crown ethers optionally having heteroatoms of group 13-17, phospha-crown ethers optionally having heteroatoms of group 13-17, crown ethers having combinations of heteroatoms of group 15-16 optionally having heteroa- toms of group 13-17 and crown ethers containing heteroatoms of group 14-17 or combinations thereof.

Suitable nitriles are those of the formula, $R^{12}C\equiv N$, where $R^{12}$ is individually selected from the group of aliphatic hydrocarbyl, halogenated aliphatic hydrocarbyl, aromatic hydrocarbyl and halogenated aromatic hydrocarbonyl residues. Preferred nitriles are acetonitrile, acrylonitrile, cyclohexanedintirile, benzonitrile, pentafluorbenzonitrile, 2,6-difluorobenzonitrile, 2,6-dichlorobenzonitrile, 2,6-dibromobenzotrile, 4-fluoro-2-trifluoromethyl benzonitrile, 3-pyridinecarbonitrile.

Suitable isonitriles are those of the formula, $R^{13}N\equiv C$, where $R^{13}$ is individually selected from the group of aliphatic hydrocarbyl, halogenated aliphatic hydrocarbyl, aromatic hydrocarbyl and halogenated aromatic hydrocarbonyl residues. A preferred isonitriles is tert-butyl isocyanide ($^{t}$BuNC), ethyl isocyanoacetate, p-toluenesulfonylmethyl isocyanide and cyclohexyl isocyanide preferably tert-butyl isonitrile ($^{t}$BuNC).

Process

The invention further relates to a process for the manufacturing of a bimetallic complex according to the present invention which comprises reacting the ligand compound of the formula (2)

(2)

wherein $R^1$ and $R^7$-$R^{10}$ have the same meaning as given above, with a metal compound represented by the formula (3)

(3)

wherein M, $R^2$-$R^6$, X, L and r and j have also the same meaning as given above. R1 in the two moieties may have the same or different meaning, preferably the same meaning.

The meaning of X for the transition metal compound of the formula (3) is already explained. Said transition metal compound in which X is a C1-10 alkyl group and/or a C7-20 aralkyl group is preferably used for the production of the bimetallic complex.

The transition metal compound represented by the formula (3) includes suitable hydrocarbyl-substituted monocyclopentadienyl metal compounds such as cyclopentadienylzirconium trimethyl, cyclopentadienylzirconium triethyl, cyclopentadienylzirconium tripropyl, cyclopentadienyltitanium trimethyl, pentamethyl-cyclopentadienyl titanium trimethyl, cyclopentadienyltitanium triphenyl, etc.; hydrocarbyloxy substituted compounds such as cyclopentadienyltitanium triiso-propoxide, cyclopentadienylzirconium tri-phenoxide, etc.; halo substituted compounds such as cyclopentadienylzirconium trichloride, indenyltitanium trichloride, pentamethylcyclopentadienylhafnium trichloride, etc.; and compounds comprising mixtures of substituents such as cyclopentadienyltitanium isopropoxide dimethyl, penta-methylcyclopentadienylzirconium methyl dichloride, (tertbutylamido)(tetramethyl-$\eta^5$-cyclopentadienyl)-1,2-ethanediylzirconium dichloride, (tert-butylamido)(tetramethyl-$\eta^5$-cyclopentadienyl)-1,2-ethanediyltitanium dichloride, (methylamido)(tetramethyl-$\eta^5$-cyclopentadienyl)-1,2-ethanediylzirconium dichloride, (methylamido)(tetramethyl-$\eta^5$-cyclopentadienyl)-1,2-ethanediyltitanium dichloride, (ethylamido)(tetramethyl-$\eta^5$-cyclopentadienyl)-methylenetitanium dichloro, (tertbutylamido)dibenzyl(tetramethyl-$\eta^5$-cyclopentadienyl)silanezirconium di benzyl, (benzylamido)dimethyl(tetramethyl-$\eta^5$-cyclopentadienyl) silanetitanium dichloride, (phenylphosphido)dimethyl(tetramethyl-$\eta^5$-cyclopentadienyl)silanezirconium dibenzyl, and the like.

The above reaction is usually carried out in an inert solvent to the reaction. Such a solvent includes, for example, aprotic solvents such as aromatic hydrocarbon solvents such as benzene, toluene and the like; aliphatic hydrocarbon solvents such as hexane, heptane and the like; ether solvents such as diethyl ether, tetrahydrofuran, 1,4-dioxane and the like; amide solvents such as hexamethylphosphoric amide, dimethylformamide and the like; polar solvents such as acetonitrile, propionitrile, acetone, diethyl ketone, methyl isobutyl ketone, cyclohexanone and the like; halogenated solvents such as dichloromethane, dichloroethane, chlorobenzene, dichlorobenzene and the like, preferably aromatic hydrocarbon solvents such as benzene, toluene and the like; aliphatic hydrocarbon solvents such as hexane, heptane and the like. One or a mixture of two or more of the solvents is used. The amount of a solvent to be used is usually in the range of 1 to 200 parts by weight, preferably 3 to 50 parts by weight relative to 1 part by weight of the ligand compound represented by the formula (2).

This reaction can be usually carried out by adding the ligand represented by the formula (2) to a solvent and then adding the transition metal compound represented by the formula (3) thereto. Thus the transition bimetallic complex represented by the formula (1) can be obtained.

The reaction temperature is usually in the range of −100° C. to the boiling point of the solvent, preferably −80 to 120° C.

Precursor

The invention further relates to a compound of the formula (2a), (2a)

wherein $R^{11}$ means iso-propyl or cyclohexyl and $R^7$ to $R^{10}$ have the same meaning as given above and wherein the two amidine moieties as in the brackets are the same or different, preferably they are the same.

The two amidine moieties of formula (2a) may be ortho-, meta- or para- to one another with respect to the aryl ring. Preferably these groups are meta- or para- to one another.

Bis-amidine compounds in which the amidine moieties are connected by an aryl ring have been described in Izvestiya Akademi Nauk, Seriya Khimicheskaya, (7), 1613-1616; 1990. Whilst the route to these compounds permitted preparation of amidines derived from the secondary amines dimethylamine, piperidine and morpholine, the route was not extended to more bulky secondary amines. Similarly bis-amidine compounds were also described in Shanxi Daxue Xuebao, Ziran Kexueban, 31(4), 561-564; 2008 but the route involved undesirable use of phosphorous containing compounds, low yields of the amidine (19%) and the route was not demonstrated with more bulky substituents such as iso-propyl groups on the amine nitrogen.

Process for Precursor

The invention further relates to a process for the manufacturing of a compound of the formula (2a) wherein the nitrile of formula (4).

(4)

wherein $R^7$-$R^{10}$ have the same meaning as given above is reacted with an organic magnesium compound $Mg(Hal)R^{11}$, wherein $R^{11}$ has the same meaning as given above, and Hal means a halide, preferably Cl, Br, I or F, in particular Br.

The reaction of an organic magnesium compound as nucleophilic agent and a dinitrile of the formula (4) is usually carried out in an inert solvent to the reaction. The ratio of magnesium amide:nitrile can range between 2:1 and 15:1; preferably the ratio is 10:1. Such a solvent includes, for example, aprotic solvents such as aromatic hydrocarbon solvents such as benzene, toluene and the like; aliphatic hydrocarbon solvents such as hexane, heptane and the like; ether solvents such as diethyl ether, tetrahydrofuran, 1,4-dioxane and the like; amide solvents such as hexamethylphosphoric amide, dimethylformamide and the like; polar solvents such as acetonitrile, propionitrile, acetone, diethyl ketone, methyl isobutyl ketone, cyclohexanone and the like; halogenated solvents such as dichloromethane, dichloroethane, chlorobenzene, dichlorobenzene and the like.

One or a mixture of two or more of the solvents is used. The amount of a solvent to be used is usually in the range of 1 to 200 times, preferably 3 to 50 times the weight of the substituted cyclopentadiene of the formula (4) or (5).

The reaction temperature is usually in the range of −100° C. to the boiling point of a solvent, preferably −80 to 120° C.

After the reaction, if needed, water is added to the resulting reaction mixture. The mixture is then separated into an organic layer and an aqueous layer to give a solution of the objective compound as the organic layer. When the organic layer and the aqueous layer cannot be easily separated due to use of a solvent compatible with water or use of a small amount of solvent in said reaction, the separation may be carried out after addition of a water-insoluble organic solvent such as toluene, ethyl acetate, chlorobenzene and the like to the reaction mixture. The imine compound represented by the formula (2a) can be purified, for example, by washing said solution of the compound with water, drying said solution, and then distilling off the solvent, and further by methods such as recrystallization, distillation, column chromatography treatment and the like.

The invention also relates to a supported catalyst which comprises a organobimetallic compound of formula (1), a supporting material and optionally a scavenger and/or an activator.

A supporting material is defined as an inorganic or organic compound that does not dissolve in the inert hydrocarbon solvent in which the process of the invention is carried out. Suitable inorganic supports include silica, magnesium halides, such as $MgF_2$, $MgCl_2$, $MgBr_2$, $MgI_2$, zeolites, and alumina. Suitable organic supports include polymers. Some non-limiting examples of polymeric supports are polyolefins such as polystryrene, polypropylene and polyethylene, polycondensates such as polyamides and polyesters and combinations thereof.

A supporting material is defined as an inorganic or organic compound that does not dissolve in the inert hydrocarbon solvent in which the process of the invention is carried out. Suitable inorganic supports include silica, magnesium halides, such as $MgF_2$, $MgCl_2$, $MgBr_2$, $MgI_2$, zeolites, and alumina. Suitable organic supports include polymers. Some non-limiting examples of polymeric supports are polyolefins such as polystryrene, polypropylene and polyethylene, polycondensates such as polyamides and polyesters and combinations thereof.

The invention further provides a catalyst system comprising
a) a bimetallic complex of the formula (1) according to the present invention and
b) an activator and
c) optionally a scavenger.

The preferred bimetallic complex of compound a) is mentioned above. A scavenger c) is a compound that reacts with impurities present in the process of the invention, which are poisonous to the catalyst.

In a preferred embodiment of the present invention the scavenger c) as of the catalyst system is a hydrocarbyl of a metal or metalloid of group 1-13 or its reaction products with at least one sterically hindered compound containing a group 15 or 16 atom.

Preferably, the group 15 or 16 atom of the sterically hindered compound bears a proton. Examples of these sterically hindered compounds are tert-butanol, iso-propanol, triphenylcarbinol, 2,6-di-tert-butylphenol, 4-methyl-2,6-di-tert-butylphenol, 4-ethyl-2,6-di-tert-butylphenol, 2,6-di-tert-butylanilin, 4-methyl-2,6-di-tert-butylanilin, 4-ethyl-2,6-di-tert-butylanilin, HMDS (hexamethyldisilazane), diisopropylamine, di-tert-butylamine, diphenylamine and the like. Some non-limiting examples of scavengers are butyllithium including its isomers, dihydrocarbylmagnesium, and hydrocarbylzinc and their reaction products with a sterically hindered compound or an acid, such as HF, HCl, HBr, HI. Furthermore organoaluminium compounds (E) as defined below can be used as activator b), in particular hydrocarbylaluminoxanes like methylaluminoxane (MAO).

Activators of the component b) for single-site catalysts are fairly well known in the art. These activators often comprise a group 13 atom, such as boron or aluminium. Examples of these activators are described in Chem. Rev., 2000, 100, 1391 by E. Y-X. Chen and T. J. Marks. A preferred activator b) is a borane (C1), a borate (C2, C3) or an organoaluminum compound (E) like alkylaluminoxane such as methyl aluminoxane (MAO). The activator for activation preferably is any boron compound of the following (C1) to (C3) and/or an organoaluminum compound (E). The organoaluminum compound (E) may be employed as a scavenger and/or an activator.

(C1) A boron compound represented by the general formula $BQ_1Q_2Q_3$ (C2) A boron compound represented by the general formula $G(BQ_1Q_2Q_3Q_4)$ (C3) A boron compound represented by the general formula (J-H)(BQ$_1$Q$_2$Q$_3$Q$_4$)
(wherein, B is a boron atom in the trivalent valence state, Q$_1$ to Q$_3$ have the same meaning as already mentioned above and Q$_4$ has the same meaning as one of the radicals Q$_1$ to Q$_3$ and Q$_1$ to Q$_4$ may be the same or different. G is an inorganic or organic cation, J is a neutral Lewis base, and (J-H) is a Bronsted acid.

In the boron compound (C1) represented by the general formula BQ$_1$Q$_2$Q$_3$, B is a boron atom in the trivalent valence state, Q$_1$ to Q$_3$ have the above mentioned meanings and may be the same or different.

Specific examples of the compound (C1) include tris (pentafluorophenyl)borane, tris(2,3,5,6-tetrafluorophenyl)borane, tris(2,3,4,5-tetrafluorophenyl)borane, tris(3,4,5-trifluorophenyl)borane, tris(2,3,4-trifluorophenyl)borane, phenyl-bis(pentafluoro-phenyl)borane and the like, and tris (pentafluorophenyl)borane is most preferable.

In the boron compound (C2) represented by the general formula G(BQ$_1$Q$_2$Q$_3$Q$_4$), G$^+$ is an inorganic or organic cation, B is a boron atom in the trivalent valence state, and Q$_1$ to Q$_4$ are as defined for Q$_1$ to Q$_3$ in the above-mentioned (C1).

Specific examples of the inorganic cation G in a compound represented by the general formula G(BQ$_1$Q$_2$Q$_3$Q$_4$) include a ferrocenium cation, alkyl-substituted ferrocenium cation, silver cation and the like, specific examples of the organic cation G thereof include a triphenylmethyl cation and the like. G is preferably a carbenium cation, and particularly preferably a triphenylmethyl cation.

Examples of (B Q$_1$Q$_2$Q$_3$Q$_4$) include tetrakis(pentafluorophenyl)borate, tetrakis(2,3,5,6-tetrafluorophenyl)borate, tetrakis(2,3,4,5-tetrafluorophenyl)borate, tetrakis(3,4,5-trifluorophenyl)borate, teterakis(2,3,4-trifluorophenyl)borate, phenyltris(pentafluoro-phenyl)borate, tetrakis(3,5-bistrifluoromethylphenyl)borate and the like.

As specific combination of them, ferroceniumtetrakis (pentafluorophenyl)borate, 1,1'-dimethylferroceniumtetrakis(pentafluorophenyl)borate, silvertetrakis(pentafluorophenyl)borate, triphenylmethyltetrakis-(pentafluorophenyl)borate, triphenylmethyltetrakis(3,5-bistrifluoromethylphenyl)borate and the like are listed, and triphenylmethyltetrakis(pentafluorophenyl)borate is most preferable.

In the boron compound (C3) represented by the general formula (J-H)$^+$(BQ$_1$Q$_2$Q$_3$Q$_4$), J is a neutral Lewis base, (J-H) is a Bronsted acid, B is a boron atom in the trivalent valence state, and Q$_1$ to Q$_4$ are as defined for Q$_1$ to Q$_4$ in the above-mentioned Lewis acid (C1).

Specific examples of the Bronsted acid (J-H)$^+$ in a compound represented by the general formula (J-H) (BQ$_1$Q$_2$Q$_3$Q$_4$) include a trialkyl-substituted ammonium, N,N-dialkylanilinium, dialkylammonium, triaryl phosphonium and the like, and as the (B Q$_1$Q$_2$Q$_3$Q$_4$), the same compounds as described above are listed. As specific combination of them, there are listed triethylammoniumtetrakis (pentafluoro-phenyl)-borate, tripropylammoniumtetrakis (pentafluorophenyl)borate, tri(n-butyl)ammonium-tetrakis (pentafluorophenyl)borate, tri(n-butyl)ammoniumtetrakis(3,5-bistrifluoromethyl-phenyl)borate, N,N-dimethylaniliniumtetrakis(pentafluoro-phenyl)borate, N,N-diethylaniliniumtetrakis(penta-fluorophenyl)borate, N,N-2,4,6-pentamethylanilinium-tetrakis(pentafluorophenyl) borate, N,N-dimethylanilinium-tetrakis(3,5-bistrifluoromethyl-phenyl)borate, di isopropyl-ammoniumtetrakis(penta-fluorophenyl)borate, dicyclohexyl-ammoniumtetrakis-(pentafluorophenyl)borate, triphenylphosphoniumtetrakis(penta-fluorophenyl)borate, tri(methylphenyl)phosphoniumtetrakis(pentafluorophenyl)borate, tri(dimethylphenyl)-phosphonium-tetrakis (pentafluorophenyl)borate and the like, and tri(n-butyl) ammonium-tetrakis(pentafluorophenyl)borate or N,N-dimethylaniliniumtetrakis(pentafluoro-phenyl)borate is most preferable.

The molar ratio of metal complex:activating cocatalyst C1-03 employed preferably ranges from 1:10 to 1:0, more preferably ranges from 1:5 to 1:0, and most preferably from 1:3 to 1:1. The exemplified ratio is 1:2

The organoaluminum compound (E) is an aluminum compound having a carbon-aluminum bond, and one or more of aluminum compounds selected from the following (E1) to (E3) are preferable.
(E1) An organoaluminum compound represented by the general formula T$^1_a$AlZ$_{3-a}$
(E2) A cyclic aluminoxane having a structure represented by the general formula $\{-Al(T^2)-O-\}_b$
(E3) Linear aluminoxane having a structure represented by the general formula T$^3\{-Al(T^3)-O-\}_c$AlT$^3_2$
(wherein, each of T$^1$, T$^2$ and T$^3$ is hydrocarbon group, and all T$^1$, all T$^2$ and all T$^3$ may be the same or different respectively. Z represents a hydrogen atom or halogen atom, and all Z's may be the same or different. 'a' represents a number satisfying 0<a≤3, 'b' is an integer of 2 or more, and 'c' is an integer of 1 or more.).

The hydrocarbon group in E1, E2 or E3 is preferably a hydrocarbon group having 1 to 8 carbon atoms, and more preferably an alkyl group.

Specific examples of the organoaluminum compound (E1) represented by the general formula T$^1_a$AlZ$_{3-a}$ include trialkylaluminums such as trimethylaluminum, triethylaluminum, tripropylaluminum, triisobutylaluminum, trihexylaluminum and the like; dialkylaluminum chlorides such as dimethylaluminum chloride, diethylaluminum chloride, dipropylaluminum chloride, diisobutylaluminum chloride, dihexylaluminum chloride and the like; alkylaluminum dichlorides such as methylaluminum dichloride, ethylaluminum dichloride, propylaluminum dichloride, isobutylaluminum dichloride, hexylaluminum dichloride and the like; dialkylaluminum hydrides such as dimethylaluminum hydride, diethylaluminum hydride, dipropylaluminum hydride, diisobutylaluminum hydride, dihexylaluminum hydride and the like; and so forth.

A preferred activator-scavenger combination is MAO/4-methyl-2,6-di-tert-butylphenol.

Specific examples of cyclic aluminoxane E2 having a structure represented by the general formula $\{-Al(T^2)-O-\}_b$ and the linear aluminoxane E3 having a structure represented by the general formula T$^3\{-Al(T^3)-O-\}_c$AlT$^3_2$ include alkyl groups such as a methyl group, ethyl group, n-propyl group, isopropyl group, n-butyl group, isobutyl group, n-pentyl group, neopentyl group and the like. b is an integer of 2 or more, c is an integer of 1 or more. Preferably, T$^2$ and T$^3$ represent a methyl group or isobutyl group, and b is 2 to 40 and c is 1 to 40.

The above-described aluminoxane is made by various methods. This method is not particularly restricted, and the aluminoxane may be produced according to a known method. For example, a solution prepared by dissolving a trialkylaluminum (for example, trimethylaluminum and the like) in a suitable organic solvent (benzene, an aliphatic hydrocarbon or the like) is allowed to contact with water to produce aluminoxane. Further, there is exemplified a method in which la trialkylaluminum (for example, trimethylaluminum and the like) is allowed to contact with a metal salt containing crystal water (for example, copper sulfate hydrate and the like) to produce aluminoxane.

The molar ratio of metal complex (1): activator/scavenger b) employed preferably ranges from 0.1:1000 to 0.1:10, more preferably ranges from 0.1:1000 to 0.1:300, and most preferably from 0.14:600 to 0.14:400.

The invention further provides a process for the polymerization of a polymer by polymerizing at least one olefinic monomer comprising contacting said monomer with a metal complex of formula (1).

Polymerization

The preferred process for polymerization is generally concluded by contacting at least one olefinic monomer with the metal complex of the formula (1) or the catalyst system according to the present invention in the gas phase, in slurry, or in solution in an inert solvent preferable a hydrocarbon solvent. Suitable solvents are in the gas phase, in slurry, or in solution in an inert solvent preferable a hydrocarbon solvent. Suitable solvents are a $C_{5-12}$ hydrocarbon such as pentane, hexane, heptane, octane, isomers and mixtures thereof, cyclohexane, methylcyclohexane, pentamethyl heptane and hydrogenated naphtha. The process of the invention may be conducted at temperatures from 10 to 250° C., depending on the product being made.

Monomer Definition

An olefinic monomer is understood to be a molecule containing at least one polymerizable double bond.

Suitable olefinic monomers are $C_{2-20}$ olefins. Preferred monomers include ethylene and $C_{3-12}$ alpha olefins which are unsubstituted or substituted by up to two $C_{1-6}$ alkyl radicals, $C_{8-12}$ vinyl aromatic monomers which are unsubstituted or substituted by up to two substituents selected from the group consisting of $C_{1-4}$ alkyl radicals, and $C_{4-12}$ straight chained or cyclic hydrocarbyl radicals which are unsubstituted or substituted by a $C_{1-4}$ alkyl radical. Illustrative non-limiting examples of such a-olefins are propylene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-hepta-decene, 1-octadecene, 1-nonadecene, 1-eicosene, 3-methyl-1-butene, 3-methyl-1-pentene, 3-ethyl-1-pentene, 4-methyl-1-pentene, 4-methyl-1-hexene, 4,4-dimethyl-1-hexene, 4,4-dimethyl-1-pentene, 4-ethyl-1-hexene, 3-ethyl-1-hexene, 9-methyl-1-decene, 11-methyl-1-dodecene and 12-ethyl-1-tetradecene. These a-olefins may be used in combination.

The monomer may also be a polyene comprising at least two double bonds. The double bonds may be conjugated or non-conjugated in chains, ring systems or combinations thereof, and they may be endocyclic and/or exocyclic and may have different amounts and types of substituents. This means that the polyene may comprise at least one aliphatic, alicyclic or aromatic group, or combinations thereof.

Suitable polyenes include aliphatic polyenes and alicyclic polyenes. More specifically, aliphatic polyenes can be mentioned, such as 1,4-hexadiene, 3-methyl-1,4-hexadiene, 4-methyl-1,4-hexadiene, 5-methyl-1,4-hexadiene, 4-ethyl-1,4-hexadiene, 1,5-hexadiene, 3-methyl-1,5-hexadiene, 3,3-dimethyl-1,4-hexadiene, 5-methyl-1,4-heptadiene, 5-ethyl-1,4-heptadiene, 5-methyl-1,5-heptadiene, 6-methyl-1,5-heptadiene, 5-ethyl-1,5-heptadiene, 1,6-heptadiene, 1,6-octadiene, 4-methyl-1,4-octadiene, 5-methyl-1,4-octadiene, 4-ethyl-1,4-octadiene, 5-ethyl-1,4-octadiene, 5-methyl-1,5-octadiene, 6-methyl-1,5-octadiene, 5-ethyl-1,5-octadiene, 6-ethyl-1,5-octadiene, 1,6-octadiene, 6-methyl-1,6-octadiene, 7-methyl-1,6-octadiene, 6-ethyl-1,6-octadiene, 6-propyl-1,6-octadiene, 6-butyl-1,6-octadiene, 1,7-octadiene, 4-methyl-1,4-nonadiene, 5-methyl-1,4-nonadiene, 4-ethyl-1,4-nonadiene, 5-ethyl-1,4-nonadiene, 5-methyl-1,5-nonadiene, 6-methyl-1,5-nonadiene, 5-ethyl-1,5-nonadiene, 6-ethyl-1,5-nonadiene, 6-methyl-1,6-nonadiene, 7-methyl-1,6-nonadiene, 6-ethyl-1,6-nonadiene, 7-ethyl-1,6-nonadiene, 7-methyl-1,7-nonadiene, 8-methyl-1,7-nonadiene, 7-ethyl-1,7-nonadiene, 1,8-nonadiene, 5-methyl-1,4-decadiene, 5-ethyl-1,4-decadiene, 5-methyl-1,5-decadiene, 6-methyl-1,5-decadiene, 5-ethyl-1,5-decadiene, 6-ethyl-1,5-decadiene, 6-methyl-1,6-decadiene, 6-ethyl-1,6-decadiene, 7-methyl-1,6-decadiene, 7-ethyl-1,6-decadiene, 7-methyl-1,7-decadiene, 8-methyl-1,7-decadiene, 7-ethyl-1,7-decadiene, 8-ethyl-1,7-decadiene, 8-methyl-1,8-decadiene, 9-methyl-1,8-decadiene, 8-ethyl-1,8-decadiene, 1,9-decadiene, 1,5,9-decatriene, 6-methyl-1,6-undecadiene, 9-methyl-1,8-undecadiene and 1,13-tetradecadiene, 1,3-butadiene, isoprene.

Alicyclic polyenes may consist of at least one cyclic fragment. Examples of these alicyclic polyenes are vinylcyclohexene, vinylnorbornene, ethylidene norbornene, dicyclopentadiene, cyclooctadiene, 2,5-norbornadiene, 1,4-divinylcyclohexane, 1,3-divinylcyclohexane, 1,3-divinylcyclopentane, 1,5-divinylcyclooctane, 1-allyl-4-vinylcyclohexane, 1,4-diallylcyclohexane, 1-allyl-5-vinylcyclooctane, 1,5-diallylcyclooctane, 1-allyl-4-isopropenylcyclohexane, 1-isopropenyl-4-vinylcyclohexane and 1-isopropenyl-3-vinylcyclopentane, and 1,4-cyclohexadiene. Preferred polyenes are polyenes having at least one endocyclic double bond and optionally at least one exocyclic double bond, such as 5-methylene-2-norbornene and 5-ethylidene-2-norbornene, 5-vinylnorbornene, and 2,5-norbornadiene, dicyclopentadiene and vinylcyclohexene.

Examples of aromatic polyenes are divinylbenzene (including its isomers), trivinyl-benzene (including its isomers) and vinylisopropenylbenzene (including its isomers).

All of the above-mentioned monomers may be further substituted with at least one group comprising a heteroatom of group 13-17, or combinations thereof.

Homopolymers, copolymers and copolymers on the basis of 3 or more of the above-mentioned olefinic monomers and also blends thereof can be prepared with the process of the present invention.

In a preferred embodiment copolymers on the basis of ethylene, at least one $C_{3-12}$ alpha olefin, preferably propylene and at least one non-conjugated diene, preferably a diene selected from the group consisting of 5-methylene-2-norbornene 5-ethylidene-2-norbornene, 5-vinylnorbornene, 2,5-norbornadiene, dicyclopentadiene (DCPD) and vinylcyclohexene, preferably from the group consisting of 5-ethylidene-2-norbornene and 5-vinylnorbornene are made with metal complex of the present invention.

The invention further relates to polymers obtainable with the metal complex of the present invention or the catalyst system of the present invention. Below, the invention will be elucidated on the basis of the following examples and comparative experiments, without being limited thereto.

EXAMPLES

Test Methods

Size Exclusion Chromatography (SEC) coupled to Refractive Index (RI) and Differential Viscometry (DV) detection.(SEC-DV)
Equipment: PL220 (Polymer Laboratories) SEC with PL220
  DRI concentration detector and
  Viscotek 220R viscometry detector.
  Detectors are operated in parallel configuration.
  Degasser: PL-DG 802
Data processing: Viscotek data processing software, TriSEC
  2.7 or higher version
Columns: PLgel Olexis (4×)
Calibration: Universal calibration with linear polyethylene
  (PE) standard (molecular weight 0.4-4000 kg/mol)

Temperature: 160° C.
Flow: 1.0 ml/min
Injection volume: 0.300 ml
Solvent/eluent: Distilled 1,2,4-trichlorobenzene with about 1 g/l of Ionol stabilizer
Sample preparation: Dissolving for 4 hours at approx. 150° C.
Filtration through 1.2 micron Ag filter
Sample concentration approx. 1.0 mg/ml
Intrinsic Viscosity (IV) was measured at 135° C. in decahydronaphtalen as solvent.
NMR ($^1$H, 300 MHz, $^{13}$C 75.4 MHz) spectra were measured on a Varian Mercury-VX 300 spectrometer.
Fourier transformation infrared spectroscopy (FT-IR), was used to determine the composition of the copolymers according to the method that is known in the art. The FT-IR measurement gives the composition of the various monomers in weight per cents relative to the total composition.

Part I: Synthesis of Ligands and Compounds

General.

All manipulations were carried out using standard Schlenk line or dry-box techniques under an atmosphere of argon or dinitrogen. Solvents were degassed by sparging with dinitrogen and dried by passing through a column of the appropriate drying agent. Toluene was refluxed over sodium and distilled. Deuterated solvents were dried over potassium ($C_6D_6$) or $P_2O_5$ ($CDCl_3$ and $CD_2Cl_2$), distilled under reduced pressure and stored under dinitrogen in Teflon valve ampoules. NMR samples were prepared under dinitrogen in 5 mm Wilmad 507-PP tubes fitted with J. Young Teflon valves. $^1$H and $^{13}$C-{$^1$H} spectra were recorded on a Varian Mercury-VX 300 spectrometer at ambient temperature unless stated otherwise and referenced internally to residual protio-solvent ($^1$H) or solvent ($^{13}$C) resonances, and are reported relative to tetramethylsilane (d=0 ppm). Assignments were confirmed using two dimensional $^1$H-$^1$H and $^{13}$C-$^1$H NMR correlation experiments. Chemical shifts are quoted in δ (ppm) and coupling constants in Hz. Mass spectra were recorded by the mass spectrometry service of the University of Oxford. IR spectra were recorded on Nicolet Magna 560E.S.P. FTIR, Perkin-Elmer 1710 or (for air-stable, solid samples) Bruker Tensor 27 FT-IR (thin film deposition on diamond ATR module) spectrometers. Air-sensitive samples were prepared in a dry-box as Nujol mulls between NaCl plates, and the data are quoted in wavenumbers (cm$^{-1}$) within the range 4000-400 cm$^{-1}$.

SYNTHESIS OF COMPOUNDS FOR THE COMPARATIVE EXAMPLES

Compound A (Me$_5$CpTiCl$_2$(NC(Ph)(iPr$_2$N)) was prepared as described for compound 6 in WO 2005/090418.

Synthesis Me$_5$CpTiMe$_2$(NC(Ph)(iPr$_2$N)) (Compound B)

To a stirring toluene (15 mL) solution of Cp*Ti{NC(Ph)N$^i$Pr$_2$}Cl$_2$ (3) (1.00 g, 2.20 mmol) was added dropwise MeLi (2.80 mL, 1.6 M in Et$_2$O, 4.40 mmol) and the resulting solution was stirred for 16 h. The volatiles were then removed in vacuo and the yellow solid was then extracted into n-hexanes (50 mL). Concentration of the solution to ca. 15 mL and subsequent storage at −30° C. for 24 h resulted in crystallisation of the desired product as large yellow crystals which were isolated and dried in vacuo. Yield=0.37 g (40%). The product was characterized by $^1$H-NMR and $^{13}$C-NMR.

Synthesis of Compounds for the Examples of the Invention

Synthesis of 1,4-C$_6$H$_4${C(NH)N$^i$Pr$_2$}$_2$ (Compound 1)

Figure 1:
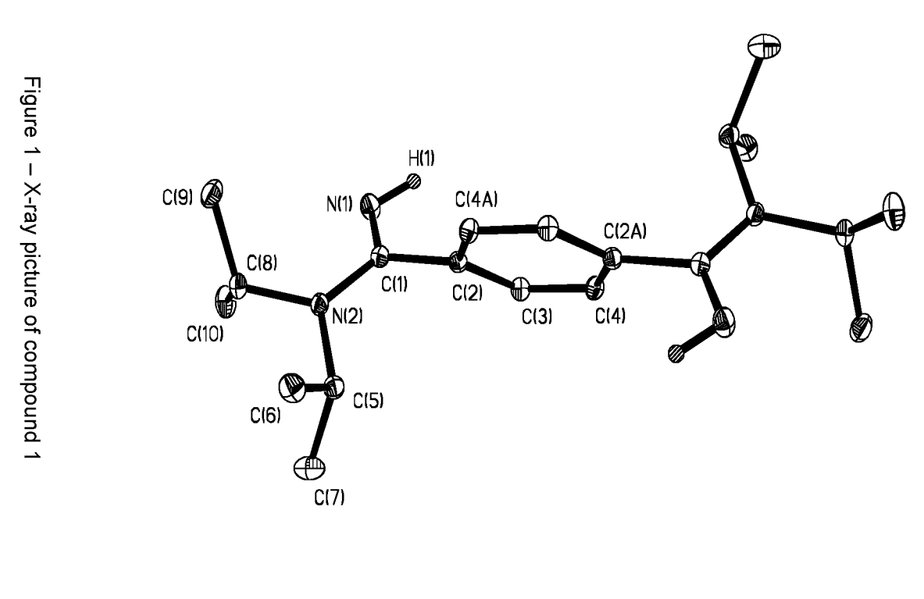
FIG. 1 shows the X-ray structure of compound 1

To a THF (250 mL) solution of diisopropylamine (73 mL, 0.52 mol) at 50° C. was added MeMgBr (140 mL, 3.0 M in diethyl ether, 0.42 mol). Following stirring at 50° C. for 3 h, the solution was cooled to 0° C. and 1,4-dicyanobenzene (5.38 g, 0.042 mol) was added. The solution was allowed to warm to RT and was stirred for a further 2 d. The mixture was cooled to 0° C. and quenched with methanol (50 mL) and then water (100 mL). The organic phase separated from the aqueous layer which was then back-extracted with dichloromethane (4×50 mL). The combined organic phases were dried over MgSO$_4$ and the volatiles removed under reduced pressure. The off-white solid was washed with pentane (3×15 mL), isolated and dried in vacuo. Yield=5.32 g (38%). Diffraction-quality crystals were grown by slow evaporation from a concentrated solution of dichloromethane. $^1$H NMR (CDCl$_3$, 299.9 MHz, 293 K): 7.21 (4H, s, Ar), 3.59 (4H, sept, N(CHMe$_2$)$_2$, $^3$J=6.6 Hz), 1.29 (24H, d, N(CHMe$_2$)$_2$, $^3$J=6.9 Hz) ppm (NH not observed). $^{13}$C{$^1$H} NMR (CDCl$_3$, 75.4 MHz, 293 K): 167.4 (CN(N$^i$Pr$_2$), 141.9 (ArC(C(N$^i$Pr$_2$)N)), 126.2 (ArCHC(C(N$^i$Pr$_2$)N)), 48.5 (N(CHMe$_2$)$_2$), 21.0 (N(CHMe$_2$)$_2$) ppm. IR (NaCl plates, Nujol mull, cm$^{-1}$): 1576 (m, $\nu_{(C=N)}$), 1225 (w), 1085 (w), 813 (w), 772 (w). ESI$^+$-HRMS: m/z=331.2857 (calcd. for [C$_{20}$H$_{35}$N$_4$]$^+$, 331.2856). Anal. found (calcd. for C$_{20}$H$_{34}$N$_4$): C, 72.47 (72.68); N, 16.87 (16.95); H, 10.49 (10.37) %.

Synthesis of 1,4-C$_6$H$_4${NC(N$^i$Pr$_2$)Cp*TiMe$_2$}$_2$ (Compound 2)

Figure 2:
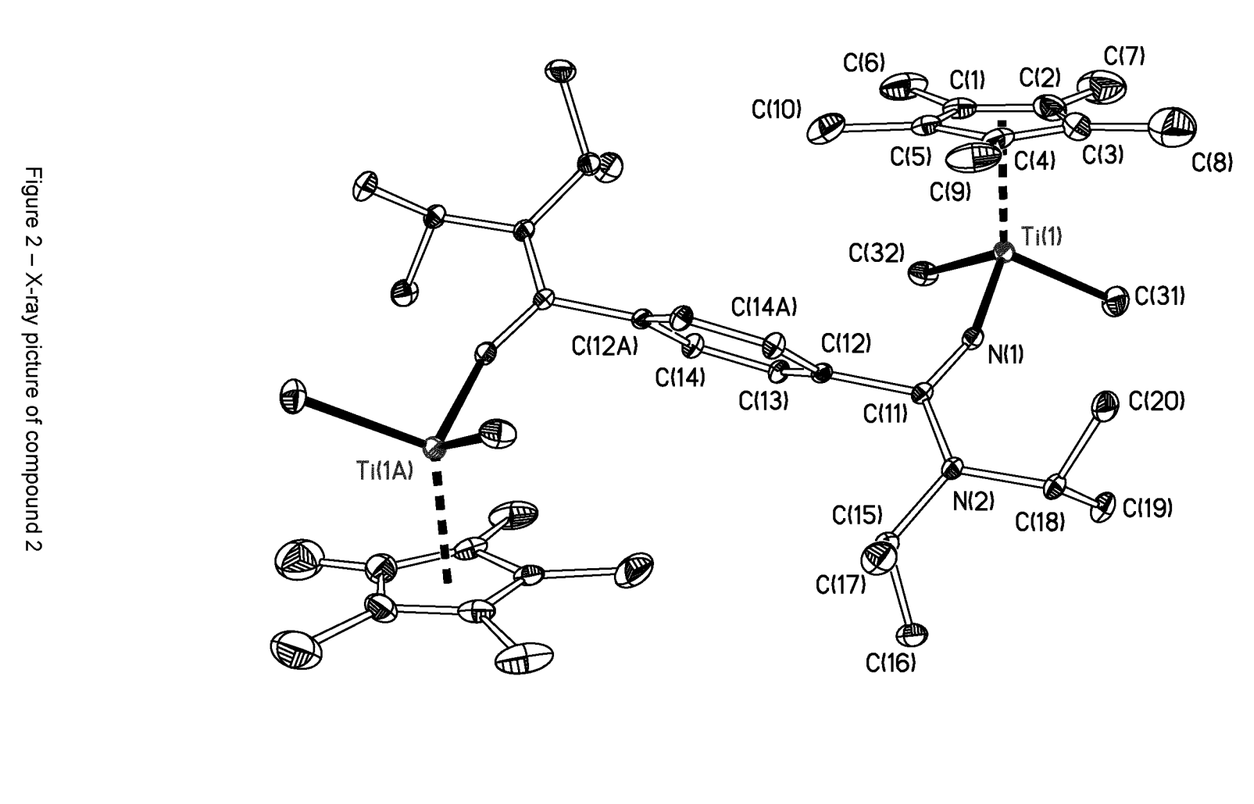
FIG. 2 shows the X-ray structure of compound 2

To a toluene (15 mL) solution of 1,4-C$_6$H$_4${C(NH)N$^i$Pr$_2$}$_2$ (compound 1) (1.01 g, 3.06 mmol) was added Cp*TiMe$_3$ (1.46 g, 6.40 mmol). The brown solution was stirred for 15 h until a precipitate appeared. After filtration the yellow solid was washed with toluene (3×15 mL) to produce a yellow solid, which was isolated and dried in vacuo. Yield=1.18 g (51%). Diffraction-quality crystals were grown by slow cooling from a concentrated solution of hot bromobenzene. $^1$H NMR (CDCl$_3$, 299.9 MHz, 223 K): 7.13 (4H, s, Ar), 3.71 (2H, sept, N(CHMe$_2$)$_2$, $^3$J=6.9 Hz), 3.51 (2H, br, N(CHMe$_2$)$_2$), 1.67 (12H, d, N(CHMe$_2$)$_2$, $^3$J=6.6 Hz), 1.64 (30H, s, C$_5$Me$_5$), 1.39 (12H, d, N(CH Me$_2$)$_2$, $^3$J=6.6 Hz), −0.19 (12H, s, TiMe) ppm. $^{13}$C{$^1$H} NMR (CDCl$_3$, 75.4 MHz, 223 K): 160.6 (CN(N$^i$Pr$_2$), 140.2 (ArC(C(N$^i$Pr$_2$)N)), 125.5 (ArCHC(C(NMe$_2$)N)), 118.9 (C$_5$Me$_5$), 51.8 (N(CHMe$_2$)$_2$), 46.6 (N(CHMe$_2$)$_2$), 45.9 (TiMe), 20.8 (N(CHMe2)$_2$), 19.9 (N(CHMe$_2$)$_2$), 11.3 (C$_5$Me$_5$) ppm. IR (NaCl plates, Nujol mull, cm$^{-1}$): 1561 (s, $\nu_{(C=N)}$), 1321 (m), 1135 (w), 890 (m), 829 (w). EI-MS: m/z=694 (3%, [M-4Me]$^+$). Anal. found (calcd. for C$_{44}$H$_{74}$N$_4$Ti$_2$): 69.85 (70.01), 9.68 (9.88), 7.57 (7.42) %.

Synthesis of 1,3-C$_6$H$_4${C(NH)N$^i$Pr$_2$}$_2$ (Compound 3)

Figure 3:
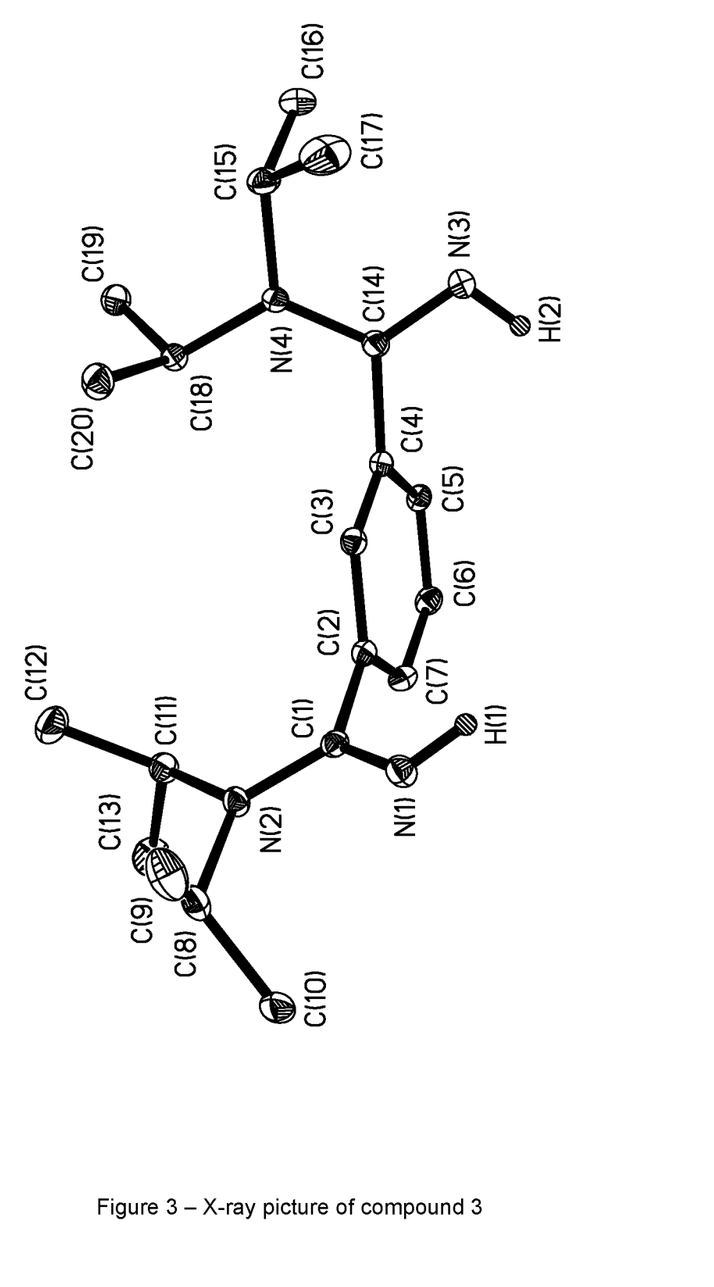
FIG. 3 shows the X-ray structure of compound 3

To a toluene (250 mL) solution of diisopropylamine (73 mL, 0.52 mol) at 50° C. was added MeMgBr (140 mL, 3.0 M in diethyl ether, 0.42 mol). Following stirring at 50° C. for 3 h, the solution was cooled to 0° C. and 1,3-dicyanobenzene (5.38 g, 0.042 mol) was added. The solution was refluxed for 13 h, cooled to 0° C., quenched with methanol (50 mL) and then water (100 mL). The organic phase was separated from the aqueous layer which was then back-extracted with dichloromethane (4×50 mL). The combined organic phases were dried over MgSO$_4$ and the volatiles removed under reduced pressure. Yield=4.20 g (30%). Diffraction-quality crystals were grown from a concentrated pentane solution at −30° C. $^1$H NMR (CDCl$_3$, 299.9 MHz, 293 K): 7.39 (1H, m, ArCHCHC(C(N$^i$Pr$_2$)N)), 7.28 (2H, m, ArCHC HC(C(N$^i$Pr$_2$)N)), 7.19 (1H, s, ArCH(C(C(N$^i$Pr$_2$)N))$_2$), 5.67 (2H, br, NH), 3.65 (4H, sept, N(CHMe$_2$)$_2$, $^3$J=6.9 Hz), 1.37 (24H, d, N(CHMe$_2$)$_2$, $^3$J=6.9 Hz) ppm. $^{13}$C{$^1$H} NMR (CDCl$_3$, 75.4 MHz, 293 K): 167.3 (CN(N$^i$Pr$_2$), 141.5 (Ar C(C(N$^i$Pr$_2$)N)), 128.7 (ArCHCHC(C(N$^i$Pr$_2$)N)), 125.5 (ArCHCHC(C(N$^i$Pr$_2$)N)), 123.4 (ArCH(C(C(N$^i$Pr$_2$)N))$_2$), 48.3 (N(CHMe$_2$)$_2$), 20.8 (N(CHMe$_2$)$_2$) ppm. IR (NaCl plates, Nujol mull, cm$^{-1}$): 1577 (s, $\nu_{(C=N)}$), 1363 (m), 1217 (m), 1027 (m), 783 (m). ESI$^+$-HRMS: m/z=331.2853 (calcd. or [C$_{20}$H$_{35}$N$_4$]$^+$, 331.2856). Anal. found (calcd. for C$_{20}$H$_{34}$N$_4$): C, 72.48 (72.68); N, 16.82 (16.95); H, 10.53 (10.37) %.

Synthesis of 1,3-C$_6$H$_4${NC(N$^i$Pr$_2$)Cp*TiMe$_2$}$_2$ (Compound 4)

Figure 4:
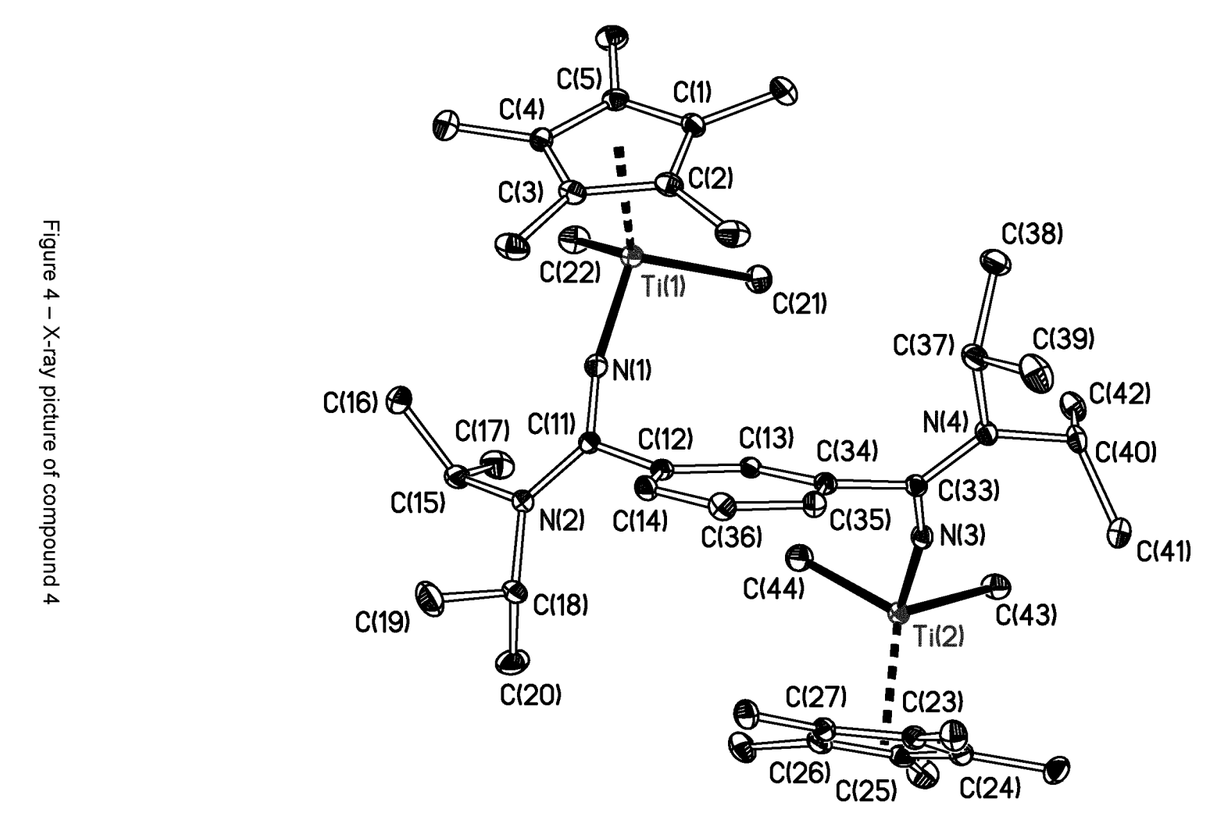
FIG. 4 shows the X-ray structure of compound 4

To a toluene (15 mL) solution of 1,3-C$_6$H$_4${C(NH)N$^i$Pr$_2$}$_2$ (compound 3) (0.50 g, 1.5 mmol) was added Cp*TiMe$_3$ (0.73 g, 3.2 mmol). The brown solution was stirred for 30 h. The volatiles were removed in vacuo to afford a yellow solid which was washed with pentane (3×15 mL) and dried in vacuo. Yield=0.52 g (46%). Diffraction-quality crystals were grown from a concentrated pentane solution at −30° C. $^1$H NMR (CDCl$_3$, 299.9 MHz, 223 K): 7.24 (1H, t, ArCHCHC(C(N$^i$Pr$_2$)N)$^3$J=7.2 Hz), 7.12 (1H, s, ArCH(C(C(N$^i$Pr$_2$)N))$_2$), 7.07 (2H, d, ArCHC HC(C(N$^i$Pr$_2$)N), $^3$J=7.5 Hz), 3.77 (2H, sept, N(CHMe$_2$)$_2$, $^3$J=6.4 Hz), 3.50 (2H, br, N(CHMe$_2$)$_2$), 1.73 (6H, d, N(CH Me$_2$)$_2$, $^3$J=6.4 Hz), 1.70 (30H, s, C$_5$Me$_5$), 1.56 (6H, d, N(CH Me$_2$)$_2$, $^3$J=6.4 Hz), 1.18 (6H, d, N(CHMe$_2$)$_2$, $^3$J=6.4 Hz), 1.13 (6H, d, N(CHMe$_2$)$_2$, $^3$J=6.4 Hz), −0.16 (12H, TiMe) ppm. $^{13}$C{$^1$H} NMR (CDCl$_3$, 75.4 MHz, 223 K): 160.2 (CN(N$^i$Pr$_2$), 141.5 (ArC(C(N$^i$Pr$_2$)N)), 127.6 (ArCHCHC(C(N$^i$Pr$_2$)N)), 124.8 (ArCHCHC(C(N$^i$Pr$_2$)N)), 123.7 (ArCH(C(C(N$^i$Pr$_2$)N))$_2$), 119.1 (C$_5$Me$_5$), 51.9 (N(CHMe$_2$)$_2$), 48.1 (TiMe), 46.9 (N(CHMe$_2$)$_2$), 45.1 (Ti Me$_2$), 21.7 (N(CHMe$_2$)$_2$), 20.9 (N(CHMe$_2$)$_2$), 20.2 (N(CH Me$_2$)$_2$), 20.0 (N(CHMe$_2$)$_2$) 11.7 (C$_5$Me$_5$) ppm. IR (NaCl plates, Nujol mull, cm$^{-1}$): 1549 (s, C=N), 1320 (m), 1036 (m), 688 (w). EI-MS: m/z=724 (25%, [M-2Me]$^+$). Anal. found (calcd. for C$_{44}$H$_{74}$N$_4$Ti$_2$): 69.65 (70.01), 9.84 (9.88), 7.42 (7.42) %.

Part II—Batch EPDM Terpolymerisations (General Procedure)

The batch copolymerizations were carried out in a 2-liter batch autoclave equipped with a double intermig and baffles. The reaction temperature was set on 90+/−3° C. and controlled by a Lauda Thermostat. The feed streams (solvents and monomers) were purified by contacting with various adsorption media to remove catalyst killing impurities such as water, oxygen and polar compounds as is known to those skilled in the art. During polymerisation the ethylene and propylene monomers were continuously fed to the gas cap of the reactor. The pressure of the reactor was kept constant by a back-pressure valve.

In an inert atmosphere of nitrogen, the reactor was filled with PMH (950 mL), MAO-10T (Crompton, 10 wt % in toluene) (450 µmol/L), BHT (900 µmol/L), 5-ethylidene-2-norbonene (ENB) (0.7 mL) and 5-vinyl-2-norbonene (VNB) (0.7 mL). The reactor was heated to 90° C., while stirring at 1350 rpm. The reactor was pressurized and conditioned under a determined ratio of ethylene, propylene and hydrogen (0.35 NL/h) After 15 minutes, the catalyst components (0.1 μmol) were added into the reactor and the catalyst vessel was rinsed with PMH (50 mL) subsequently. After 10 minutes of polymerisation, the monomer flow was stopped and the solution was carefully dumped in an Erlenmeyer flask of 2 L, containing a solution of Irganox-1076 in iso-propanol and dried over night at 100° C. under reduced pressure. The polymers were analysed for intrinsic viscosity (IV), for molecular weight distribution (SEC-DV) and composition (FT-IR).

The level of long chain branching of the polymers was determined using Dynamic Mechanical Spectrometry (DMS) experiments and expressed by the so-called delta-delta value (Δδ) which is used as a measure of the non-Newtonian viscoelastic behaviour of EPDM polymers. The Δδ parameter is defined as the difference between the phase angle, δ, at frequencies of $10^{-1}$ rad/s and $10^2$ rad/s as derived from frequency sweep plots obtained in a DMS experiment at 125° C. The presence of branched polymer chains will decrease the δ value specifically at low frequencies while the the δ value at high frequencies is dependent primarily of the average molecular weight of the polymer. As a result the Δδ value decreases with increasing long chain branching.

The experimental results are given in table 1

TABLE 1

| Example | Metal-organic Compound | Yield (g) | Incorporated C2 (wt %) | ENB (wt %) | VNB (wt %) | IV (dl/g) | Mw (kg/mol) | Mz (kg/mol) | Mw/Mn | Δδ/° |
|---|---|---|---|---|---|---|---|---|---|---|
| 1 | 2 | 11.95 | 42.5 | 0.69 | 0.43 | 2.0 | 195 | 480 | 2.6 | 46.0 |
| 2 | 2 | 11.81 | 47.7 | 0.71 | 0.44 | 2.3 | — | — | — | 44.1 |
| 3 | 4 | 3.40 | 47.7 | 0.68 | 0.43 | 2.3 | 205 | 410 | 2.4 | 45.7 |
| 4 | 4 | 2.77 | 45.1 | 0.63 | 0.41 | 2.1 | — | — | — | 45.9 |
| 5 | B | 8.02 | 49.6 | 1.07 | 0.74 | 2.8 | 275 | 565 | 2.4 | 42.0 |
| 6 | B | 7.66 | 47.5 | 1.04 | 0.74 | 2.7 | — | — | — | 43.3 |

C3 feed=400 NL/h; C2 feed=200 NL/h; ENB feed=0.7 ml; VNB feed=0.7 ml; H2 feed=0.35 NL/h; T=90° C.; P=7 barg The conditions of the polymerization were designed to minimize long chain branching effects in each case maximizing the capability of each catalyst to produce polymer with as little branching as possible. The table shows that very similar polymer properties (C2 incorporation, polymer molecular weight, PDI). The DMS (Δδ) measurements observed for compounds 2, 4 and B revealed higher Δδ values for the invented catalysts (2 and 4) compared to catalyst B meaning less long chain branching evident in the invented catalysts 2 and 4 compared to catalyst B.

The invention claimed is:

1. A bimetallic complex of the formula (1)

(1)

having two cyclopentadienyl-amidinato-metal-containing moieties as in the brackets, wherein:

M is a group 4-6 metal;

$R^1$ is a substituent comprising nitrogen, through which $R^1$ is bonded to the imine carbon atom;

$R^2$-$R^6$ are the same or different, and each represents a hydrogen atom, an optionally substituted C1-10 alkyl group, an optionally substituted C1-10 alkoxy group, an optionally substituted C6-20 aryl group, an optionally substituted C6-20 aryloxy group, an optionally substituted C7-20 aralkyl group, an optionally substituted C7-20 aralkyloxy group, a silyl group substituted with optionally substituted C1-20 hydrocarbon group(s), a C1-20 hydrocarbon-substituted amino group, or the adjacent $R^2$-$R^6$ are optionally linked to each other to form a ring;

$R^7$-$R^{10}$ are the same or different, and each represents a hydrogen atom, a halogen atom, an optionally substituted C1-10 alkyl group, an optionally substituted C1-10 alkoxy group, an optionally substituted C6-20 aryl group, an optionally substituted C6-20 aryloxy group, an optionally substituted C7-20 aralkyl group, an optionally substituted C7-20 aralkyloxy group, a silyl group substituted with optionally substituted C1-20 hydrocarbon group(s), a C1-20 hydrocarbon-substituted amino group, or the adjacent $R^7$-$R^{10}$ are optionally linked to each other to form a ring;

L is an optional neutral Lewis basic ligand, and j is an integer denoting the number of neutral ligands L; and X is an anionic ligand, and r is an integer denoting the number of anionic ligands X, and wherein the two cyclopentadienyl-amidinato-metal-containing moieties are the same or different.

2. The bimetallic complex according to claim 1, wherein M is selected from the group consisting of Ti, Zr and Hf.

3. The bimetallic complex according to claim 1, wherein $R^2$-$R^6$ are the same or different and each represents a hydrogen atom or a C1-5 alkyl group.

4. The bimetallic complex according to the claim 1, wherein each X independently represents a halogen atom, a C1-10 alkyl group, a C7-20 aralkyl group, a C6-20 aryl group or a C1-20 hydrocarbon-substituted amino.

5. The bimetallic complex according to claim 1, wherein j is zero.

6. The bimetallic complex according to claim 1, wherein $R^7$-$R^{10}$ are each a hydrogen atom.

7. A process for producing the bimetallic complex represented by the formula (1) according to claim 1, the process comprising:

reacting a ligand compound of the formula (2)

wherein $R^1$ and $R^7$-$R^{10}$ have the same meaning as given in claim 1, with a metal compound represented by the formula (3)

wherein M, $R^2$-$R^6$, X, L and r and j have also the same meaning as given in claim 1.

8. A catalyst system comprising
a) a metal complex of the formula (1) according to claim 1, and
b) an activator.

9. The catalyst system according to claim 8, further comprising a scavenger c), wherein the scavenger c) is hydrocarbyl of a metal or metalloid of group 1-13 or its reaction products with at least one sterically hindered compound containing a group 15 or 16 atom.

10. The catalyst system according to claim 8, wherein the activator b) is a borane, a borate, or an organoaluminum compound.

11. A process for the preparation of a polymer by polymerizing at least one olefinic monomer, the process comprising contacting at least one olefinic monomer with the catalyst system according to claim 8.

12. The process according to claim 11, wherein the at least one olefinic monomer comprises ethylene and at least a $C_3$-$C_{12}$-α-olefin.

13. The process according to claim 11, wherein the at least one olefinic monomer comprises ethylene, at least one $C_{3-12}$ alpha olefin, and at least one non-conjugated diene.

14. The process according to claim 13, wherein the at least one non-conjugated diene is selected from the group consisting of 5-methylene-2-norbornene, 5-ethylidene-2-norbornene, 5-vinylnorbornene, 2,5-norbornadiene, dicyclopentadiene, and vinylcyclohexene.

15. The bimetallic complex according to claim 1, wherein:
M is selected from the group consisting of Ti, Zr and Hf;
$R^2$-$R^6$ are the same or different and each represents a hydrogen atom or a C1-5 alkyl group;
each X independently represents a halogen atom, a C1-10 alkyl group, a C7-20 aralkyl group, a C6-20 aryl group, or a C1-20 hydrocarbon-substituted amino;
j is zero; and
$R^7$-$R^{10}$ are each a hydrogen atom.

16. The bimetallic complex according to claim 1, wherein:
M is Ti;
$R^2$-$R^6$ are methyl;
each X independently is Cl or methyl;
j is zero; and
$R^7$-$R^{10}$ are each a hydrogen atom.

17. A bimetallic complex of the formula (1)

having two identical, or two different moieties as in the brackets,
wherein:
M is a group 4-6 metal;
$R^1$ is a substituent comprising a heteroatom of group 15, through which $R^1$ is bonded to the imine carbon atom;
$R^2$-$R^6$ are the same or different and each represents a hydrogen atom, an optionally substituted C1-10 alkyl group, an optionally substituted C1-10 alkoxy group, an optionally substituted C6-20 aryl group, an optionally substituted C6-20 aryloxy group, an optionally substituted C7-20 aralkyl group, an optionally substituted C7-20 aralkyloxy group, a silyl group substituted with optionally substituted C1-20 hydrocarbon groups), a C1-20 hydrocarbon-substituted amino group or the adjacent $R^2$-$R^6$ may be linked to each other to form a ring;
$R^7$-$R^{10}$ are the same or different and each represents a hydrogen atom, a halogen atom, an optionally substituted C1-10 alkyl group, an optionally substituted C1-10 alkoxy group, an optionally substituted C6-20 aryl group, an optionally substituted C6-20 aryloxy group, an optionally substituted C7-20 aralkyl group, an optionally substituted C7-20 aralkyloxy group, a silyl group substituted with optionally substituted C1-20 hydrocarbon group(s), a C1-20 hydrocarbon-substituted amino group or the adjacent $R^7$-$R^{10}$ may be linked to each other to form a ring;
L is an optional neutral Lewis basic ligand, and j is an integer denoting the number of neutral ligands L; and
X is an anionic ligand, and r is an integer denoting the number of anionic ligands X.

* * * * *